(12) United States Patent
Chittoor et al.

(10) Patent No.: US 11,970,704 B2
(45) Date of Patent: Apr. 30, 2024

(54) PLANT REGULATORY ELEMENTS AND USES THEREOF

(71) Applicant: Monsanto Technology LLC, St. Louis, MO (US)

(72) Inventors: Jaishree M. Chittoor, Wildwood, MO (US); Stanislaw Flasinski, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 91 days.

(21) Appl. No.: 17/238,858

(22) Filed: Apr. 23, 2021

(65) Prior Publication Data

US 2021/0332378 A1    Oct. 28, 2021

Related U.S. Application Data

(60) Provisional application No. 63/016,904, filed on Apr. 28, 2020.

(51) Int. Cl.
*C12N 15/82* (2006.01)

(52) U.S. Cl.
CPC ..... *C12N 15/8271* (2013.01); *C12N 15/8216* (2013.01); *C12N 2310/141* (2013.01); *C12N 2320/50* (2013.01); *C12N 2330/50* (2013.01)

(58) Field of Classification Search
CPC .................................................. C12N 15/8271
USPC .......................................................... 435/419
See application file for complete search history.

(56) References Cited

U.S. PATENT DOCUMENTS

2017/0183674 A1    6/2017    Flasinski

OTHER PUBLICATIONS

Vettore et al. Genet. Mol. Biol. 24:1-4 (Year: 2001).*
Invitation to Pay Additional Search Fees for PCT/US21/28920 dated Aug. 11, 2021.
International Search Report and Written Opinion regarding International App. No. PCT/US21/28920, dated Oct. 13, 2021.

* cited by examiner

*Primary Examiner* — Li Zheng
(74) *Attorney, Agent, or Firm* — Dentons US LLP; Judith Koehler

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

16 Claims, No Drawings
Specification includes a Sequence Listing.

PLANT REGULATORY ELEMENTS AND USES THEREOF

REFERENCE TO RELATED APPLICATION

This application claims the benefit of U.S. Provisional Application No. 63/016,904, filed Apr. 28, 2020, which is herein incorporated by reference in its entirety.

INCORPORATION OF SEQUENCE LISTING

The sequence listing that is contained in the file named "MONS481US-sequence_listing.txt", is 13,550 bytes [bytes](as measured in Microsoft Windows®), was created on Apr. 22, 2021, and is filed herewith by electronic submission and incorporated by reference herein.

FIELD OF THE INVENTION

The invention relates to the field of plant molecular biology and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides gene regulatory elements for use in plants. The invention also provides recombinant DNA molecules comprising the regulatory elements. The present invention also provides transgenic plant cells, plants, and seeds comprising the regulatory elements. In one embodiment, the regulatory elements are operably linked to a transcribable DNA molecule. In certain embodiments, the transcribable DNA molecule may be heterologous with respect to the regulatory sequence. Thus, a regulatory element sequence provided by the invention may, in particular embodiments, be defined as operably linked to a heterologous transcribable DNA molecule. The present invention also provides methods of using the regulatory elements and making and using the recombinant DNA molecules comprising the regulatory elements, and the transgenic plant cells, plants, and seeds comprising the regulatory elements operably linked to a transcribable DNA molecule.

Thus, in one aspect, the invention provides a recombinant DNA molecule comprising a DNA sequence selected from the group consisting of: (a) a sequence with at least about 85 percent sequence identity to any of SEQ ID NOs:1-5; (b) a sequence comprising any of SEQ ID NOs:1-5; and (c) a fragment of any of SEQ ID NOs:1-5, wherein the fragment has gene-regulatory activity; wherein the sequence is operably linked to a heterologous transcribable DNA molecule. By "heterologous transcribable DNA molecule," it is meant that the transcribable DNA molecule is heterologous with respect to the polynucleotide sequence to which it is operably linked. In specific embodiments, the recombinant DNA molecule comprises a DNA sequence having at least about 85 percent, at least about 86 percent, at least about 87 percent, at least about 88 percent, at least about 89 percent, at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-5.

In another aspect, provided herein are transgenic plant cells comprising a recombinant DNA molecule comprising a DNA sequence selected from the group consisting of: (a) a sequence with at least about 85 percent sequence identity to any of SEQ ID NOs:1-5; (b) a sequence comprising any of SEQ ID NOs:1-5; and (c) a fragment of any of SEQ ID NOs:1-5, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs:1-5; b) a sequence comprising any of SEQ ID NOs:1-5; and c) a fragment of any of SEQ ID NOs:1-5, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided.

In another aspect, the invention provides a method of producing a commodity product comprising obtaining a transgenic plant or part thereof containing a recombinant DNA molecule of the invention and producing the commodity product therefrom. In one embodiment, the commodity product is seeds, processed seeds, protein concentrate, protein isolate, starch, grains, plant parts, seed oil, biomass, flour and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE SEQUENCES

SEQ ID NO:1 is a DNA sequence of a regulatory expression element group or EXP, EXP-ANDge.Ubq:5 comprised of a promoter (P-ANDge.Ubq:7), operably linked 5' to leader (L-ANDge.Ubq:2), operably linked 5' to an intron (I-ANDge.Ubq:2) derived from *Andropogon gerardii*.

SEQ ID NO:2 is a DNA sequence of a promoter, P-ANDge.Ubq:7 derived from *Andropogon gerardii*.

SEQ ID NO:3 is a DNA sequence of a leader or 5' UTR, L-ANDge.Ubq:2 derived from *Andropogon gerardii*.

SEQ ID NO:4 is a DNA sequence of an intron, I-ANDge.Ubq:2 derived from *Andropogon gerardii*.

SEQ ID NO:5 is a DNA sequence of a 3' UTR, T-ARUdo.TubA:1 derived from *Arundo donax*.

SEQ ID NO:6 is a DNA sequence of an EXP, EXP-CaMV.35S+Zm.DnaK:12.

SEQ ID NO:7 is a DNA sequence of a 3' UTR, T-Sb.Nltp4-1:1:2 derived from *Sorgum bicolor*.

SEQ ID NO:8 is a synthetic coding sequence optimized for plant expression for ß-glucuronidase (GUS, GOI- Ec.uidA+St.LS1.nno:1) with a processable intron derived from the potato light-inducible, tissue-specific St-LS1 gene (Genbank Accession: X04753).

DETAILED DESCRIPTION OF THE INVENTION

The invention provides regulatory elements having gene-regulatory activity in plants. The nucleotide sequences of these regulatory elements are provided as SEQ ID NOs:1-5. These regulatory elements are capable of affecting the expression of an operably linked transcribable DNA molecule in plant tissues, and therefore regulating gene expression of an operably linked transgene in transgenic plants. The invention also provides methods of modifying, producing, and using recombinant DNA molecules which contain the provided regulatory elements. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:1-5.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs:1-5, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering.

As used herein, a "regulatory expression element group" or "EXP" sequence may refer to a group of operably linked regulatory elements, such as enhancers, promoters, leaders, and introns. For example, a regulatory expression element group may be comprised, for instance, of a promoter operably linked 5' to a leader sequence, operably linked 5' to an intron sequence. An EXP useful in practicing the present invention is presented as SEQ ID NO:1.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene, or for the purposes of this disclosure, promoters provided herein are comprised of a promoter operably linked 5' to the leader. Alternately, promoters may be synthetically produced or manipulated DNA molecules. Promoters may also be chimeric. Chimeric promoters are produced through the fusion of two or more heterologous DNA molecules. A promoter useful in practicing the present invention is presented as SEQ ID NOs:2, or fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters, or in combination with other expression elements and expression element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. Methods for producing such fragments from a starting promoter molecule are well known in the art.

Compositions derived the promoter element of SEQ ID NO:2 such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from the promoter element of SEQ ID NOs:2, comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. The promoter element provided as SEQ ID NO:2 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. A leader useful in practicing the present invention is presented as SEQ ID NO:3 or fragments or variants thereof. In specific embodiments, such DNA sequences may be defined as being capable of acting as a leader in a host cell, including, for example, a transgenic plant cell. In one embodiment, such sequences are decoded as comprising leader activity.

The leader sequence (also referred to as a 5' UTR) of SEQ ID NO:3 may be comprised of regulatory elements, or may adopt secondary structures that can have an effect on transcription or translation of an operably linked transcribable DNA molecule. The leader sequence of SEQ ID NO:3 can be used in accordance with the invention to make chimeric regulatory elements that affect transcription or translation of a an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements. An exemplary intron useful in practicing the present invention is presented as SEQ ID NO:4.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region, wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. Second, the 3' UTR should not cause a reduction in the transcriptional activity imparted by the promoter, leader, enhancers, and introns that are used to drive expression of the DNA molecule. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. A 3' UTR useful in practicing the present invention is presented as SEQ ID NO:5.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention. Enhancers can be derived from the promoter presented as SEQ ID NO:2.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments for example, the fusion of a promoter to an enhancer element. Thus, the design, construction, and use of chimeric promoters according to the methods disclosed herein for modulating the expression of operably linked transcribable DNA molecules are encompassed by the present invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:1-5 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites and/or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, a polynucleotide sequence provided as SEQ ID NOs:1-5 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a recombinant DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404, however other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences, those encoding guide RNAs, and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs:1-5, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, augmented carbon sequestration, and desirable biofuel production.

Examples of genes of agronomic interest known in the art include those for herbicide resistance (U.S. Pat. Nos. 6,803, 501; 6,448,476; 6,248,876; 6,225,114; 6,107,549; 5,866, 775; 5,804,425; 5,633,435; and 5,463,175), increased yield (U.S. RE38,446; U.S. Pat. Nos. 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573;

6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. RE37,543; U.S. Pat. Nos. 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. An example of a selectable marker transgene is provided as SEQ ID NO:8.

Genome Editing

Several embodiments relate to a recombinant DNA construct comprising an expression cassette(s) comprising a sequence with at least about 85 percent sequence identity to any of SEQ ID NOs:1-5 or a fragment thereof operably linked to a heterologous DNA sequence encoding a site-specific genome modification enzyme and/or any associated protein(s) to carry out genome modification. These nuclease-expressing cassette(s) may be present in the same molecule or vector as a donor template for templated editing (in cis) or on a separate molecule or vector (in trans). Several methods for editing are known in the art involving different sequence-specific genome modification enzymes (or complexes of proteins and/or guide RNA) that modify the genomic DNA. In some embodiments, a site-specific genome modification enzyme modifies the genome by inducing a double-strand break (DSB) or nick at a desired genomic site or locus. In some embodiments, during the process of repairing the DSB or nick introduced by the genome modification enzyme, a donor template DNA may become integrated into the genome at the site of the DSB or nick. In some embodiments, during the process of repairing the DSB or nick introduced by the genome modification enzyme, an insertion or deletion mutation (indel) may be introduced into the genome. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases, reverse transcriptases and any combination thereof.

Several embodiments relate to a gene regulatory element as described herein operably linked to a heterologous transcribable DNA molecule encoding one or more components of a genome editing system. Genome editing systems may be used to introduce one or more insertions, deletions, substitutions, base modifications, translocations, or inversions to a genome of a host cell. In some embodiments, a gene regulatory element as described herein is operably linked to a heterologous transcribable DNA molecule encoding a sequence-specific DNA binding domain, such as a CRISPR-Cas effector protein, a zinc finger protein, or a transcription activator (TAL) protein. In some embodiments, the sequence-specific DNA binding domain maybe a fusion protein. In some embodiments, a gene regulatory element as described herein is operably linked to a heterologous transcribable DNA molecule encoding a CRISPR-Cas effector protein. In some embodiments, the CRISPR-Cas effector protein is selected from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a gene regulatory element as described herein is operably linked to a heterologous transcribable DNA molecule encoding a guide RNA. As used herein, a "guide RNA" or "gRNA" refers to an RNA that recognizes a target DNA sequence and directs, or "guides", a CRISPR effector protein to the target DNA sequence. A guide RNA is comprised of a region that is complementary to the target DNA (referred to as the crRNA) and a region that binds the CRISPR effector protein (referred to as the tracrRNA). A guide RNA may be a single RNA molecule (sgRNA) or two separate RNAs molecules (a 2-piece gRNA). In some embodiments a gRNA may further comprise an RNA template (pegRNA) for a reverse transcriptase.

Several embodiments relate to a gene regulatory element as described herein operably linked to a heterologous transcribable DNA molecule encoding one or more components of a CRISPR-Cas genome editing system comprising a CRISPR-Cas effector protein and a guide RNA. Examples of CRISPR-Cas effector proteins include, but are not limited to, Cas9, C2c1, C2c3, C2c4, C2c5, C2c8, C2c9, C2c10, Cas12a (also referred to as Cpf1), Cas12b, Cas12c, Cas12d, Cas12e, Cas12h, Cas12i, Cas12g, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), Csf5, Cas14a, Cas14b, and Cas14c effector protein. In some embodiments, a gene regulatory element as described herein is operably linked to a CRISPR-Cas effector protein comprising a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation. In some embodiments, a gene regulatory element as described herein is operably linked to a CRISPR-Cas effector protein having a mutation in its nuclease active site to generate a nickase activity operably linked to a reverse transcriptase enzyme.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the recombinant DNA molecule of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, CA, 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique,* (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen.

Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-5. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of the Regulatory Elements

This Example describes the identification, synthesis, and cloning of regulatory expression elements derived from *Andropogon gerardii* (Big blue stem) and *Arundo donax* (Giant reed).

A novel ubiquitin regulatory element was identified and isolated from genomic DNA of the monocot species *Andropogon gerardii* (Big blue stem). The 5' untranslated region (5' UTR) of each of the Ubiquitin 1 transcripts was used to design primers to amplify the corresponding regulatory elements for the identified Ubiquitin gene, which comprises a promoter, leader (5' UTR), and first intron operably linked. The primers were used with GenomeWalker™ (Clontech Laboratories, Inc, Mountain View, CA) libraries constructed following the manufacturer's protocol to clone the 5' region of the corresponding genomic DNA sequence.

In addition, a novel 3' UTR was identified and isolated from genomic DNA of the monocot species *Arundo donax* (Giant reed). The identified EXP and its corresponding promoter, leader and intron from *Andropogon gerardii* and the 3' UTR from *Arundo donax* are presented in Table 1.

TABLE 1

Regulatory expression element group, promoter, leader, intron, and 3' UTR.

| Annotation | SEQ ID NO: | Size (bp) | Description and/or regulatory elements of EXP linked in 5' → 3' direction (SEQ ID NOs): |
|---|---|---|---|
| EXP-ANDge.Ubq:5 | 1 | 2006 | EXP: P-ANDge.Ubq:7 (SEQ ID NO: 2); L-ANDge.Ubq:2 (SEQ ID NO: 3); I-ANDge.Ubq:2 (SEQ ID NO: 4) |
| P-ANDge.Ubq:7 | 2 | 851 | Promoter |
| L-ANDge.Ubq:2 | 3 | 154 | Leader |
| I-ANDge.Ubq:2 | 4 | 1001 | Intron |
| T-ARUdo.TubA:1 | 5 | 498 | 3' UTR |

The identified EXP and 3' UTRs were synthesized and cloned using methods known in the art into binary plants transformation vector constructs, in an expression cassette used to drive ß-glucuronidase (GUS) expression to assess their activity in stably transformed corn plants, as described in Examples 2 and 3.

Example 2

Analysis of EXP-ANDge.Ubq:5 Driving GUS Expression in Stably Transformed Corn Plants Corn plants were transformed with a vector, specifically a plant expression vector containing the EXP, EXP-ANDge.Ubq:5 driving expression of the β-glucuronidase (GUS) transgene. The resulting plants were analyzed for GUS protein expression, to assess the effect of the regulatory element group (EXP) on expression and compared with a standard control EXP.

Corn plants were transformed with a plant GUS expression construct. The EXP, EXP-ANDge.Ubq:5 (SEQ ID NO:1) was cloned into a base plant expression vector using standard methods known in the art. The resulting plant expression vector contained a left border region from *Agrobacterium tumefaciens* (B-AGRtu.left border), a first transgene selection cassette used for selection of transformed plant cells that confers resistance to the herbicide glyphosate, a second transgene cassette to assess the activity of EXP-ANDge.Ubq:5 comprised of a transgene cassette comprising EXP-ANDge.Ubq:5 (SEQ ID NO:1) operably linked 5' to a coding sequence for GUS comprised of a processable intron (SEQ ID NO:8), operably linked to a 3' UTR (T-Sb.Nltp4-1:1:2, SEQ ID NO:7), and a right border region from *Agrobacterium tumefaciens* (B-AGRtu.right border). The GUS expression driven by EXP-ANDge.Ubq:5 was compared to expression of a control construct similar to that above comprising a GUS transgene expression cassette comprised of the EXP, EXP-CaMV.35S+Zm.DnaK:12 (SEQ ID NO:6) operably linked 5' to the GUS coding sequence, operably linked to the 3' UTR, T-Sb.Nltp4-1:1:2.

Corn plant cells were transformed using the binary transformation vector constructs described above by *Agrobacterium*-mediated transformation, as is well known in the art. The resulting transformed plant cells were induced to form whole corn plants.

Qualitative and quantitative GUS analysis was used to evaluate expression element activity in selected plant organs and tissues in transformed plants. For qualitative analysis of GUS expression by histochemical staining, whole-mount or sectioned tissues were incubated with GUS staining solution containing 1 mg/mL of X-Gluc (5-bromo-4-chloro-3-indolyl-b-glucuronide) for 5 h at 37° C. and de-stained with 35% EtOH and 50% acetic acid. Expression of GUS was qualitatively determined by visual inspection of selected plant organs or tissues for blue coloration under a dissecting or compound microscope.

For quantitative analysis of GUS expression by enzymatic assays, total protein was extracted from selected tissues of transformed corn plants. One to two micrograms of total protein was incubated with the fluorogenic substrate, 4-methyleumbelliferyl-β-D-glucuronide (MUG) at 1 mM concentration in a total reaction volume of 50 microliters. After 1 h incubation at 37° C., the reaction was stopped by adding 350 microliters of 200 mM sodium bicarbonate solution. The reaction product, 4-methlyumbelliferone (4-MU), is maximally fluorescent at high pH, where the hydroxyl group is ionized. Addition of the basic sodium carbonate solution simultaneously stops the assay and adjusts the pH for quantifying the fluorescent product 4-MU. The amount of 4-MU formed was estimated by measuring its fluorescence using a FLUOstar Omega Microplate Reader (BMG LABTECH) (excitation at 355 nm, emission at 460 nm). GUS activity values are provided in nmoles of 4-MU/hour/mg total protein.

The following tissues were sampled for GUS expression in the $R_0$ generation: V4 stage Leaf and Root; V7 stage Leaf and Root; VT stage Leaf, Flower/Anther, and Pollen; R1 stage Cob/Silk; and R3 stage Seed Embryo and Seed Endosperm 21 days after pollination (DAP). Table 2 shows the mean quantitative GUS expression for the sampled tissues.

As can be seen in Table 2, the EXP, EXP-ANDge.Ubq:5 (SEQ ID NO:1) provided an expression profile that is quite distinct from that of the control, EXP-CaMV.35S+Zm.DnaK:12 (SEQ ID NO:6). For example, expression driven by EXP-ANDge.Ubq:5 in the VT anther and pollen was higher than that driven by EXP-CaMV.35S+Zm.DnaK:12. While expression in the leaf driven by EXP-CaMV.35S+Zm.DnaK:12 appeared to increase from V4 to V7 stage and then decline by VT stage; expression in the leaf, driven by EXP-ANDge.Ubq:5 remained consistent throughout all three stages. Expression driven by EXP-ANDge.Ubq:5 was higher in R1 cob/silk in comparison to the control. EXP-ANDge.Ubq:5 (SEQ ID NO:1) demonstrates unique characteristics of expression and provides a new tool for expression of selected transgenes.

Example 3

The 3' UTR, T-ARUdo.TubA:1 Modulates GUS Expression in Stably Transformed Corn Plants Corn plants were transformed with a vector, specifically a plant expression vector containing the 3' UTR, T-ARUdo.TubA:1 modulating the expression of the β-glucuronidase (GUS) transgene. The resulting plants were analyzed for GUS protein expression, to assess the effect of the 3' UTR regulatory element on expression.

Corn plants were transformed with a plant GUS expression construct and a control construct. The constructs were similar to those described above in Example 2. Both constructs comprised the EXP, EXP-CaMV.35S+Zm.DnaK:12 (SEQ ID NO:6), operably linked 5' to a coding sequence for GUS comprised of a processable intron (SEQ ID NO:8). The control construct was as described above in Example 2, wherein the GUS coding sequence was operably linked to the 3' UTR, T-Sb.Nltp4-1:1:2. The other construct used the 3' UTR, T-ARUdo.TubA:1 (SEQ ID NO:5) to terminate transcription of the GUS transgene.

Corn plants were transformed and GUS expression was assayed as described in Example 2. The following tissues were sampled for GUS expression in the $R_0$ generation: V4 stage Leaf and Root; V7 stage Leaf and Root; VT stage Leaf, Flower/Anther, and Pollen; R1 stage Cob/Silk; and R3 stage Seed Embryo and Seed Endosperm 21 days after pollination (DAP). Table 3 shows the mean quantitative GUS expression for the sampled tissues and the fold enhancement of GUS provided by T-ARUdo.TubA:1.

TABLE 2

Mean GUS expression of stably transformed corn plants.

| | | EXP-CaMV.35S + Zm. DnaK:12/T-Sb.Nltp4 | | EXP-ANDge.Ubq: 5/T-Sb.Nltp4 | |
| --- | --- | --- | --- | --- | --- |
| Stage | Organ | Mean | Std Err | Mean | Std Err |
| V4 | Leaf | 866.3 | 316.54 | 166.48 | 18.22 |
| | Root | 435.76 | 117.99 | 294.21 | 46.88 |
| V7 | Leaf | 1263.29 | 462.27 | 114.19 | 7.65 |
| | Root | 78.74 | 23.43 | 168.6 | 17.62 |
| VT | Flower/Anther | 432.22 | 131.1 | 769.11 | 93.96 |
| | Flower/Pollen | 135.93 | 90.25 | 1639.32 | 365.6 |
| | Leaf | 27.82 | 4.99 | 152.24 | 13.98 |
| R1 | Cob/Silk | 157.75 | 102.89 | 668.4 | 54.19 |
| R3 | Seed Embryo | 97.31 | 21.03 | 370.87 | 36.06 |
| | Seed Endosperm | 225.49 | 49.42 | 284.3 | 29.15 |

TABLE 3

Mean GUS expression of stably transformed corn plants.

| | | EXP-CaMV.35S + Zm.DnaK: 12/T-Sb.Nltp4 | | EXP-CaMV.35S + Zm.DnaK: 12/T-ARUdo.TubA | | Increase in Expression from |
| --- | --- | --- | --- | --- | --- | --- |
| Stage | Organ | Mean | Std Err | Mean | Std Err | T-ARUdo.TubA:1 |
| V4 | Leaf | 866.3 | 316.54 | 3560.14 | 706.91 | 4.1 |
| | Root | 435.76 | 117.99 | 3014.71 | 576.41 | 6.9 |
| V7 | Leaf | 1263.29 | 462.27 | 5708.89 | 837.17 | 4.5 |
| | Root | 78.74 | 23.43 | 7380.5 | 1110.24 | 93.7 |
| VT | Flower/Anther | 432.22 | 131.1 | 2524.12 | 347.64 | 5.8 |
| | Flower/Pollen | 135.93 | 90.25 | 1431.6 | 606.06 | 10.5 |
| | Leaf | 27.82 | 4.99 | 4918.45 | 754.58 | 176.8 |
| R1 | Cob/Silk | 157.75 | 102.89 | 5258.4 | 737.62 | 33.3 |
| R3 | Seed Embryo | 97.31 | 21.03 | 1042.5 | 132.46 | 10.7 |
| | Seed Endosperm | 225.49 | 49.42 | 1281.12 | 146.97 | 5.7 |

As can be seen in Table 3, the 3' UTR, T-ARUdo.TubA:1 (SEQ ID NO:5) enhanced expression of the GUS transgene in every tissue assayed when compared to the 3' UTR, T-Sb.Nltp4-1:1:2. Transcript analysis showed proper termination and polyadenylation of the GUS mRNA. In some instances, the enhancement of transgene expression was quite large. For example, expression in the VT leaf was 176.8 fold greater in than in the control. V7 root expression was 93.7 fold higher than in the control. Thus, the 3' UTR, T-ARUdo.TubA:1 (SEQ ID NO:5), provides an enhancement of transgene expression relative to the control.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
   a) a sequence comprising any of SEQ ID NOs:1, 2 and 4; and
   b) a fragment comprising at least 200 contiguous nucleotides of any of SEQ ID NOs:1, 2 and 4, wherein the fragment has promoter activity;
   wherein said sequence is operably linked to a heterologous transcribable DNA molecule.

2. The recombinant DNA molecule of claim 1, wherein said sequence comprises the DNA sequence of any of SEQ ID NOs:1, 2 and 4.

3. The recombinant DNA molecule of claim 1, wherein the DNA sequence comprises gene regulatory activity.

4. The recombinant DNA molecule of claim 1, wherein the heterologous transcribable DNA molecule comprises a gene of agronomic interest.

5. The recombinant DNA molecule of claim 4, wherein the gene of agronomic interest confers herbicide tolerance in plants.

6. The recombinant DNA molecule of claim 4, wherein the gene of agronomic interest confers pest resistance in plants.

7. The recombinant DNA molecule of claim 1, wherein the heterologous transcribable DNA molecule encodes a dsRNA, an miRNA, or a siRNA.

8. A transgenic plant cell comprising the recombinant DNA molecule of claim 1.

9. The transgenic plant cell of claim 8, wherein said transgenic plant cell is a monocotyledonous plant cell.

10. The transgenic plant cell of claim 8, wherein said transgenic plant cell is a dicotyledonous plant cell.

11. A transgenic plant, or part thereof, comprising the recombinant DNA molecule of claim 1.

12. A progeny plant of the transgenic plant of claim 11, or a part thereof, wherein the progeny plant or part thereof comprises said recombinant DNA molecule.

13. A transgenic seed, wherein the seed comprises the recombinant DNA molecule of claim 1.

14. A method of producing a commodity product comprising obtaining a transgenic plant or part thereof according to claim 11 and producing the commodity product therefrom.

15. The method of claim 14, wherein the commodity product is selected from the group consisting of seeds, processed seeds, protein concentrate, protein isolate, starch, grains, plant parts, seed oil, biomass, flour and meal.

16. A method of expressing a transcribable DNA molecule comprising obtaining a transgenic plant according to claim 11 and cultivating plant, wherein the transcribable DNA is expressed.

* * * * *

SEQUENCE LISTING

<160> NUMBER OF SEQ ID NOS: 8

<210> SEQ ID NO 1
<211> LENGTH: 2006
<212> TYPE: DNA
<213> ORGANISM: Andropogon gerardii
<220> FEATURE:
<221> NAME/KEY: misc_feature
<222> LOCATION: (1)..(2006)
<223> OTHER INFORMATION: A DNA sequence of an EXP, EXP-ANDge.Ubq:5
      comprised of P-ANDge.Ubq:7, operably linked 5' to L-ANDge.Ubq:2,
      operably linked 5' to I-ANDge.Ubq:2.

<400> SEQUENCE: 1

```
tccaagttct tgtggcttct tattttgttt aaattgttaa aactgaaaaa tgtccctagg      60
cctctaaaaa ctttgagaaa actcatataa aatattttg gtacatgaga aaccctaaaa     120
aaatatttag aacacatgaa agtatctata aaagcttaaa aagaatttat cataagaaac     180
atggagacag tatccagaaa agttataaaa tttccacaaa catttaatga atatgtaaac     240
atgtttggaa aaactttcca caacaaaacc atgagatgca ataatcgtac acattttca      300 agattttttt gaatattttt ccatttccta gagctaaata caacttttgg aagcttttac     360
agatacttcc atgagattta aatatttatt tccattttca tgtatcacat atctttagat     420
tttttttcta ggagcttta taagcttaga gatattttca cttttacaa ccttattata      480 gttttcttat tttaactaaa aaataaaata tttttaaaaa acacttctaa tctgaacggg     540
catggaggta ttttaaatta taactaacga gtagaccact actacaactt tttccttttt     600
tctatagaaa tgaggatagt tttttttta aatggaggaa tgaggatagg tactgaagcc      660
caagtcgtcg ttttcgagat tgggctgtat agcctcttaa acaaggaatc ggacctcaaa     720
agcccatcac ggaactgccc tgctgttatc ggtgttggag agcgtgtcca aatggttcca     780
gaggctgtgt ggtggggctg gattgcgcca cggcctcatg ttcgctgcgc gatttctggt     840
tgccttgatg aggcgcaggt gggcccctcc gttgcccagg ataaaagtcc acttccggcc     900
tccggtttcc ccaatccatc agccgccacc gatcccaatc gtgagttctc cgcaccatcg     960
gcacgcagac gaaggaagca aggctctacc gatcgtctct tgaaggtaca ctcttcctcg    1020
attcgtcaac ctcgatttag gaggtacact cttcctcgat tcgtcaacct cgatttgcct    1080
aagcgtgtat ggtcggttct cgaatctcga ttccccgcat agcgtgtatg gtcgattgaa    1140
cgtgtatggt cgattttcga atctcgattt tggattctga tgtcttccct tttacttatg    1200
atttgatgta tcacatagct taatagattc tgcaccgatc tgttacttat gatttgattg    1260
attggttgct tgttgcgttc cacaaaggac ggtgctattt tctgttctgg aacgagatca    1320
tgtagatatt atatagttag ggttccaatt caaaaggttg attagtgtat tataaaaatt    1380
aaaagggcta aatcgttcct atcatgttgt ctcgagcgta atcctgcagg tatcatagaa    1440
ttatgtttga attcaataga ttgatcggtg tatcatttaa atcaaggcta aatcactaca    1500
```

| | |
|---|---|
| cttctgttgc tacagagcac aatcctgtag gtatcttatc ttagaattaa gttttgataa | 1560 |
| attaattagt gtattttttta gaacaaattg attagtatat tattgtcaaa ttgagaaggt | 1620 |
| taaatcatgc ctaccatgtt gtctccgttt gtgatcatat tagtcagaag gatatgcata | 1680 |
| aatcttctgc taaacttatt tgttgttag cccctttcaga tttttatgtt gaatcctttc | 1740 |
| tctatatttg ctgcttgtat atgttgaatc gtcatgctaa ttgcaaatgt aattagcata | 1800 |
| ttggcagttg gtatatgcat cttcctaatc tggatggatg cagtgttgta gtatgttcta | 1860 |
| atgcatggtt catcaaattt tgtctgtatt cacttttgt tgcctctgtt ccatagttga | 1920 |
| gacttgaatc attattttct gagcactatg tttttctaca cctattatgg tagcttacca | 1980 |
| tgtgactttt gcctctgcag gtgcag | 2006 |

<210> SEQ ID NO 2
<211> LENGTH: 851
<212> TYPE: DNA
<213> ORGANISM: Andropogon gerardii
<220> FEATURE:
<221> NAME/KEY: misc_feature
<222> LOCATION: (1)..(851)
<223> OTHER INFORMATION: A DNA sequence of a promoter, P-ANDge.Ubq:7.

<400> SEQUENCE: 2

| | |
|---|---|
| tccaagttct tgtggcttct tattttgttt aaattgttaa aactgaaaaa tgtccctagg | 60 |
| cctctaaaaa ctttgagaaa actcatataa aatattttg gtacatgaga aaccctaaaa | 120 |
| aaatatttag aacacatgaa agtatctata aaagcttaaa aagaatttat cataagaaac | 180 |
| atggagacag tatccagaaa agttataaaa tttccacaaa catttaatga atatgtaaac | 240 |
| atgtttggaa aaactttcca caacaaaacc atgagatgca ataatcgtac acatttttca | 300 |
| agatttttt gaatattttt ccattcctta gagctaaata caacttttgg aagcttttac | 360 |
| agatacttcc atgagattta aatatttatt tccattttca tgtatcacat atctttagat | 420 |
| ttttttttcta ggagctttta taagcttaga gatattttca cttttttacaa ccttattata | 480 |
| gttttcttat tttaactaaa aaataaaata ttttttaaaaa acacttctaa tctgaacggg | 540 |
| catggaggta ttttaaatta taactaacga gtagaccact actacaactt tttccttttt | 600 |
| tctatagaaa tgaggatagt tttttttttta aatggaggaa tgaggatagg tactgaagcc | 660 |
| caagtcgtcg ttttcgagat tgggctgtat agcctcttaa acaaggaatc ggacctcaaa | 720 |
| agcccatcac ggaactgccc tgctgttatc ggtgttggag agcgtgtcca aatggttcca | 780 |
| gaggctgtgt ggtggggctg gattgcgcca cggcctcatg ttcgctgcgc gatttctggt | 840 |
| tgccttgatg a | 851 |

<210> SEQ ID NO 3
<211> LENGTH: 154
<212> TYPE: DNA
<213> ORGANISM: Andropogon gerardii
<220> FEATURE:
<221> NAME/KEY: misc_feature
<222> LOCATION: (1)..(154)
<223> OTHER INFORMATION: A DNA sequence of a 5' UTR or leader,
      L-ANDge.Ubq:2.

<400> SEQUENCE: 3

| | |
|---|---|
| ggcgcaggtg ggcccctccg ttgcccagga taaaagtcca cttccggcct ccggtttccc | 60 |
| caatccatca gccgccaccg atcccaatcg tgagttctcc gcaccatcgg cacgcagacg | 120 |
| aaggaagcaa ggctctaccg atcgtctctt gaag | 154 |

<210> SEQ ID NO 4
<211> LENGTH: 1001
<212> TYPE: DNA
<213> ORGANISM: Andropogon gerardii
<220> FEATURE:
<221> NAME/KEY: misc_feature
<222> LOCATION: (1)..(1001)
<223> OTHER INFORMATION: A DNA sequence of an intron, I-ANDge.Ubq:2.

<400> SEQUENCE: 4

```
gtacactctt cctcgattcg tcaacctcga tttaggaggt acactcttcc tcgattcgtc    60
aacctcgatt tgcctaagcg tgtatggtcg gttctcgaat ctcgattccc cgcatagcgt   120
gtatggtcga ttgaacgtgt atggtcgatt ttcgaatctc gattttggat tctgatgtct   180
tccctttac ttatgatttg atgtatcaca tagcttaata gattctgcac cgatctgtta   240
cttatgattt gattgattgg ttgcttgttg cgttccacaa aggacggtgc tattttctgt   300
tctggaacga gatcatgtag atattatata gttagggttc caattcaaaa ggttgattag   360
tgtattataa aaattaaaag ggctaaatcg ttcctatcat gttgtctcga gcgtaatcct   420
gcaggtatca tagaattatg tttgaattca atagattgat cggtgtatca tttaaatcaa   480
ggctaaatca ctacacttct gttgctacag agcacaatcc tgtaggtatc ttatcttaga   540
attaagtttt gataaattaa ttagtgtatt ttttagaaca aattgattag tatattattg   600
tcaaattgag aaggttaaat catgcctacc atgttgtctc cgtttgtgat catattagtc   660
agaaggatat gcataaatct tctgctaaac ttatttgttg tttagccctt tcagattttt   720
atgttgaatc ctttctctat atttgctgct tgtatatgtt gaatcgtcat gctaattgca   780
aatgtaatta gcatattggc agttggtata tgcatcttcc taatctggat ggatgcagtg   840
ttgtagtatg ttctaatgca tggttcatca aattttgtct gtattcactt tttgttgcct   900
ctgttccata gttgagactt gaatcattat tttctgagca ctatgttttt ctacacctat   960
tatggtagct taccatgtga cttttgcctc tgcaggtgca g                      1001
```

<210> SEQ ID NO 5
<211> LENGTH: 498
<212> TYPE: DNA
<213> ORGANISM: Arundo donax
<220> FEATURE:
<221> NAME/KEY: misc_feature
<222> LOCATION: (1)..(498)
<223> OTHER INFORMATION: A DNA sequence of a 3' UTR, T-ARUdo.TubA:1.

<400> SEQUENCE: 5

```
atgcttcctg gtgctccgtc aggcctgtgt gccgctgcta tcctatgatc tgcccgagtg    60
gctcgtatcc gttatgtgtc tgtttgcttg aactatcagt cgttgtgtgt ggtatggtac   120
tatggtttac aacacctgat gttgtaagac ttgttatgtt taatccccgc tttgctactg   180
ggttattatg aacatcgtta tggttgtaac atttggtgct cttttttttt actttctgct   240
gagttaatgt tgctgaggac ggccttgacg cctgataaat tttctgtgcc gtctgttatc   300
accgctttgc ccactgtttt gtccctcatg cgagggagac tattcgtggt attaaccagt   360
gcttttctgt cgatgctaac cagtgctttt ctgtcgatgc taatctccag tgacagtagt   420
tgtacccatt ccagttggtt gcttccagtc tttgccacct cttaatgtga cattgtcaaa   480
gcagttcccc gtgtttgt                                                 498
```

<210> SEQ ID NO 6

<211> LENGTH: 1670
<212> TYPE: DNA
<213> ORGANISM: Artificial
<220> FEATURE:
<223> OTHER INFORMATION: A DNA sequence of an EXP,
      EXP-CaMV.35S+Zm.DnaK:12.

<400> SEQUENCE: 6

```
agattagcct tttcaatttc agaaagaatg ctaacccaca gatggttaga gaggcttacg     60
cagcaggtct catcaagacg atctacccga gcaataatct ccaggaaatc aaataccttc    120
ccaagaaggt taaagatgca gtcaaaagat tcaggactaa ctgcatcaag aacacagaga    180
aagatatatt tctcaagatc agaagtacta ttccagtatg gacgattcaa ggcttgcttc    240
acaaaccaag gcaagtaata gagattggag tctctaaaaa ggtagttccc actgaatcaa    300
aggccatgga gtcaaagatt caaatagagg acctaacaga actcgccgta agactggcg    360
aacagttcat acagagtctc ttacgactca atgacaagaa gaaaatcttc gtcaacatgg    420
tggagcacga cacacttgtc tactccaaaa atatcaaaga tacagtctca gaagaccaaa    480
gggcaattga gacttttcaa caaagggtaa tatccggaaa cctcctcgga ttccattgcc    540
cagctatctg tcactttatt gtgaagatag tggaaaagga aggtggctcc tacaaatgcc    600
atcattgcga taaggaaag gccatcgttg aagatgcctc tgccgacagt ggtcccaaag    660
atggaccccc acccacgagg agcatcgtgg aaaaagaaga cgttccaacc acgtcttcaa    720
agcaagtgga ttgatgtgat atctccactg acgtaaggga tgacgcacaa tcccactatc    780
cttcgcaaga cccttcctct atataaggaa gttcatttca tttggagagg cacgggggga    840
ctctagagga tccactagtc ggaccgaccg tcttcggtac gcgctcactc cgccctctgc    900
ctttgttact gccacgtttc tctgaatgct ctcttgtgtg gtgattgctg agagtggttt    960
agctggatct agaattacac tctgaaatcg tgttctgcct gtgctgatta cttgccgtcc   1020
tttgtagcag caaatatag ggacatggta gtacgaaacg aagatagaac ctacacagca   1080
atacgagaaa tgtgtaattt ggtgcttagc ggtatttatt taagcacatg ttggtgttat   1140
agggcacttg gattcagaag tttgctgtta atttaggcac aggcttcata ctacatgggt   1200
caatagtata gggattcata ttataggcga tactataata atttgttcgt ctgcagagct   1260
tattatttgc caaaattaga tattcctatt ctgttttgt ttgtgtgctg ttaaattgtt   1320
aacgcctgaa ggaataaata taaatgacga aattttgatg tttatctctg ctcctttatt   1380
gtgaccataa gtcaagatca gatgcacttg ttttaaatat tgttgtctga agaaataagt   1440
actgacagta ttttgatgca ttgatctgct tgtttgttgt aacaaaattt aaaaataaag   1500
agtttccttt ttgttgctct ccttacctcc tgatggtatc tagtatctac caactgacac   1560
tatattgctt ctctttacat acgtatcttg ctcgatgcct tctccctagt gttgaccagt   1620
gttactcaca tagtctttgc tcatttcatt gtaatgcaga taccaagcgg              1670
```

<210> SEQ ID NO 7
<211> LENGTH: 487
<212> TYPE: DNA
<213> ORGANISM: Sorghum bicolor
<220> FEATURE:
<221> NAME/KEY: misc_feature
<222> LOCATION: (1)..(487)
<223> OTHER INFORMATION: A DNA sequence of a 3' UTR, T-Sb.Nltp4-1:1:2.

<400> SEQUENCE: 7

```
tgatcgatca taaggacatg catgaggcat gctcgttgga tggcgatcag catgcagtcg     60
```

| | |
|---|---:|
| tcgttgtttt accagatgtc gtccatgact ccctccatgg atgatgcatg caatgagata | 120 |
| gatacataaa ttaaggagta gatcatgcat gcaccgtacc tgttagtgat cactccgttt | 180 |
| aattagtatt tactgtttac taccttgagt ttacaccaac tctgtcgtcg ctgtggctgt | 240 |
| cgtcgtgtac ctcgatcgta cgtgtgtgtg tgtagcaggc tagcaaagca gcactcaacg | 300 |
| tcgtccttgg gggtttgctt gcctttaacc ttgttgcttt agcacacagg tttctgaata | 360 |
| atgaatacta ctagcttttg tgtccattat atatatattg tactgtatgc atgatgtttt | 420 |
| ccatccatga gtcatgagag tgatgtgttc aagtaataag atatagtaac atatacacgc | 480 |
| gacgtac | 487 |

<210> SEQ ID NO 8
<211> LENGTH: 2001
<212> TYPE: DNA
<213> ORGANISM: Artificial
<220> FEATURE:
<223> OTHER INFORMATION: A synthetic coding sequence optimized for plant
      expression for beta-glucuronidase (GUS, GOI-Ec.uidA+St.LS1.nno:1)
      with a processable intron derived from the potato light-inducible,
      tissue-specific St-LS1 gene (Genbank Accession: X04753).

<400> SEQUENCE: 8

| | |
|---|---:|
| atggtgaggc ccgttgagac cccgactagg gagatcaaga agctggacgg cctctgggcc | 60 |
| ttctccctcg accgtgagaa ctgcggcatc gaccagcgct ggtgggagtc cgccctccag | 120 |
| gagtctaggg ccatcgccgt gcccggttcc ttcaacgacc agttcgccga cgccgacatc | 180 |
| cgcaactacg cgggcaacgt ctggtatcag cgcgaggtgt tcatcccgaa gggctgggcg | 240 |
| ggccagcgca tcgtgctccg cttcgacgcc gtgacccact acggcaaggt ctgggtgaac | 300 |
| aatcaggagg taagttttctg cttctaccett tgatatatat ataataatta tcattaatta | 360 |
| gtagtaatat aatatttcaa atatttttttt caaaataaaa gaatgtagta tatagcaatt | 420 |
| gcttttctgt agtttataag tgtgtatatt ttaatttata acttttctaa tatatgacca | 480 |
| aaatttgttg atgtgcaggt gatggagcac cagggcggtt acaccccgtt cgaggccgac | 540 |
| gtgacgccgt acgtgatcgc cgggaagtcc gtccgcatca ccgtctgcgt gaacaatgag | 600 |
| ctgaactggc agaccatccc gcctggcatg gtcatcaccg acgagaacgg caagaagaag | 660 |
| cagtcctact ccacgacttc ttcaactac gctggcatcc accgctccgt gatgctctac | 720 |
| accactccca cacctgggt ggacgacatc accgtggtca cccacgtggc ccaggactgc | 780 |
| aaccacgcct ccgtggactg gcaagtcgtt gccaacggcg acgtcagcgt cgagctgcgc | 840 |
| gacgccgacc agcaagtcgt tgccaccggc cagggcacca gcggcaccct ccaagtcgtc | 900 |
| aaccctcacc tctggcagcc tggcgagggc tacctctacg agctgtgcgt caccgccaag | 960 |
| agccagactg agtgcgacat ctaccctctc cgcgtcggca tcaggagcgt cgctgtcaag | 1020 |
| ggcgagcagt tcctcatcaa ccacaagcct ttctacttca ctggtttcgg ccgccacgag | 1080 |
| gacgctgacc tgaggggcaa gggtttcgac aacgtcctga tggtccacga ccacgctctg | 1140 |
| atggactgga tcgtgccaa cagctacagg accagtcact acccgtacgc tgaggagatg | 1200 |
| ctggactggg ctgacgagca cggtatcgtc gtgatcgacg agactgctgc ggtcggtttc | 1260 |
| aacctgtctc tgggcattgg tttcgaggct gggaacaagc cgaaggagct gtactctgag | 1320 |
| gaagctgtca acggcgagac tcagcaagct catctccagg cgattaagga gctgattgcc | 1380 |
| agggacaaga accatccgtc tgtcgtgatg tggtctattg cgaatgagcc ggacaccaga | 1440 |
| ccgcaagggg cgcgtgaata cttcgcgccg ctggcggagg cgactcgcaa actggaccca | 1500 |

-continued

```
acccgtccaa tcacgtgcgt caatgtcatg ttctgcgacg cccatacgga tacgatctcg  1560
gacctgttcg atgttctttg tctcaatcgg tactatgggt ggtatgttca gagcggggat  1620
cttgagacgg cggagaaggt tcttgagaag gaactcctgg cgtggcaaga gaagctccat  1680
cagccgatca ttatcacgga gtacggggtt gacacacttg cgggccttca cagtatgtac  1740
acagatatgt ggtcggagga ataccagtgt gcatggttgg atatgtacca tcgtgtcttc  1800
gaccgggttt cagcggttgt cggcgaacaa gtctggaact tcgcagactt cgccacgagc  1860
caagggatac tgcgggtagg agggaacaag aagggaatct tcacacggga tcggaagccc  1920
aagtcagcag ccttcctgtt gcagaagcga tggacaggaa tgaacttcgg agaaaagcca  1980
cagcaaggcg gaaagcagtg a                                             2001
```